(12) United States Patent
Accardi et al.

(10) Patent No.: US 7,080,095 B2
(45) Date of Patent: Jul. 18, 2006

(54) MEDICAL DIAGNOSTIC SYSTEM REMOTE SERVICE METHOD AND APPARATUS

(75) Inventors: Kenneth Lawrence Accardi, Pewaukee, WI (US); Kevin James Jay, Whitefish Bay, WI (US); Diane Marie Miesbauer, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 848 days.

(21) Appl. No.: 09/224,262

(22) Filed: Dec. 31, 1998

(65) Prior Publication Data

US 2003/0014425 A1    Jan. 16, 2003

(51) Int. Cl.
*G06F 7/00* (2006.01)
*G06F 15/16* (2006.01)

(52) U.S. Cl. .................... 707/104.1; 709/200

(58) Field of Classification Search ............... 600/300, 600/483–485, 437; 324/309; 705/2–3; 378/118; 707/104.1
See application file for complete search history.

(56) References Cited

U.S. PATENT DOCUMENTS

| | | | |
|---|---|---|---|
| 4,838,275 A * | 6/1989 | Lee | 600/483 |
| 5,012,411 A * | 4/1991 | Policastro et al. | 600/485 |
| 5,603,323 A | 2/1997 | Pflugrath et al. | 128/660.01 |
| 5,655,084 A | 8/1997 | Pinsky et al. | 395/203 |
| 5,675,744 A | 10/1997 | Tsujii | 395/203 |
| 5,715,823 A | 2/1998 | Wood et al. | 128/660.01 |
| 5,790,793 A | 8/1998 | Higley | 395/200.48 |
| 5,938,607 A * | 8/1999 | Jago et al. | 600/437 |
| 6,198,283 B1 * | 3/2001 | Foo et al. | 324/309 |
| 6,206,829 B1 * | 3/2001 | Iliff | 600/300 |
| 6,212,256 B1 * | 4/2001 | Miesbauer et al. | 378/118 |
| 6,434,572 B1 * | 8/2002 | Derzay et al. | 707/104.1 |

* cited by examiner

*Primary Examiner*—Uyen Le
*Assistant Examiner*—Susan Y. Chen
(74) *Attorney, Agent, or Firm*—Fletcher Yoder

(57) ABSTRACT

A system for providing remote service to medical diagnostic systems is described that includes a field service unit connectable to an automated service facility via a network link. The field service unit is configured to compose service requests based upon a series or menu of predefined service modules or functions. The service request includes identification of a diagnostic system or facility of interest. The request is communicated to the automated service facility which verifies the request and executes the requested function. Data may be gathered from the diagnostic system or institution as well as from service databases. Results of the service operation are automatically transmitted to the requesting service unit.

28 Claims, 3 Drawing Sheets

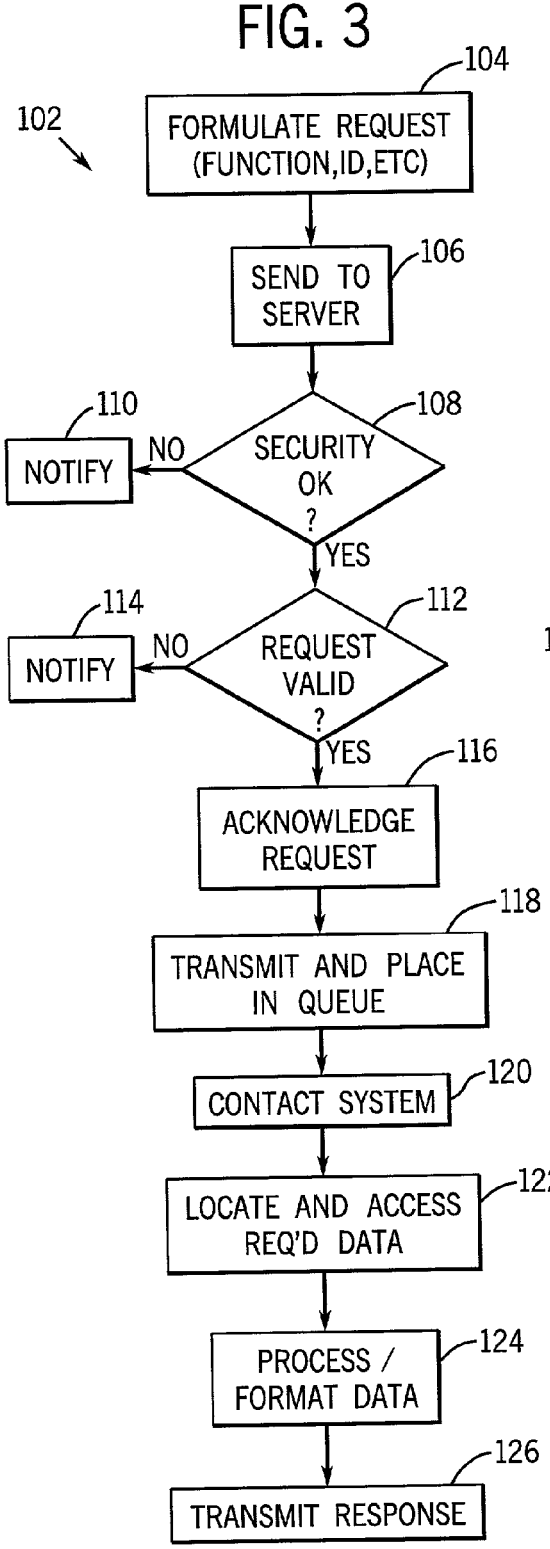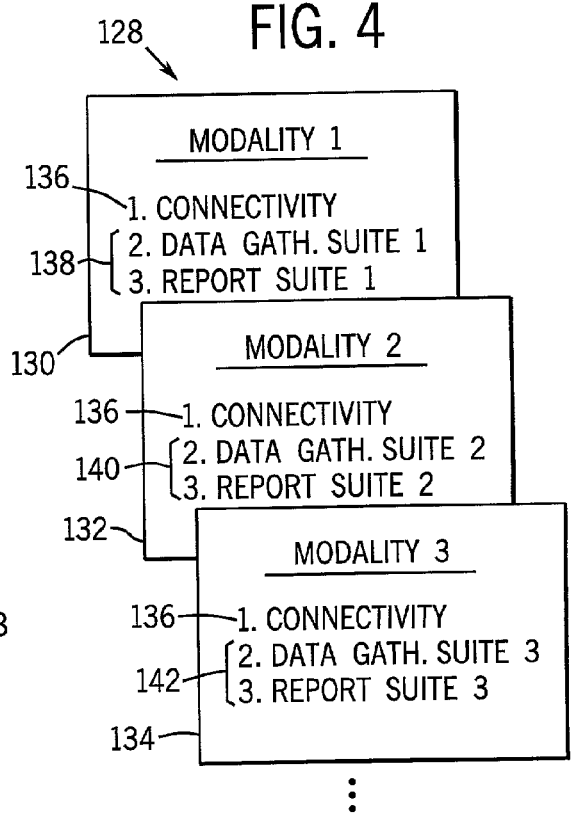

MEDICAL DIAGNOSTIC SYSTEM REMOTE SERVICE METHOD AND APPARATUS

FIELD OF THE INVENTION

The present invention relates generally to the field of medical diagnostic systems, including imaging systems, image archiving and retrieval systems, and the like. More particularly, the invention relates to a technique for providing remote service to such systems via network connections that permit remote field service requests to be generated and communicated to a service center, and therethrough to be relayed to networked diagnostic equipment. The technique also permits responses to service requests or data requests to be channeled back through the networked system to a requesting field service unit.

BACKGROUND OF THE INVENTION

In the field of medical diagnostic systems, a variety of system types are known and are presently in use. In general, diagnostic systems are categorized by modality, the various modalities generally being grouped by the underlying physics involved in acquisition of image data and reconstruction of the data into a useful image. Imaging modalities presently available include magnetic resonance imaging (MRI) systems, computed tomography (CT) imaging systems, conventional and digital x-ray systems, positron emission tomography (PET) systems, ultrasound systems, and so forth. In addition to these imaging systems, modem diagnostic facilities often include other diagnostic equipment such as picture archive and communication systems (PACS) for storing digitized images and for retrieving and communicating the images as desired. Medical facilities may include one or more different modality machines, as well as one or more PACS stations. In larger facilities, the modality systems and the PACS stations may be networked to fully integrate work flow.

Due to the demanding schedules often imposed on medical diagnostic systems of the type described above, it is often important that the systems remain in proper working order and available when needed. Accordingly, it has become customary to provide highly trained service personnel for monitoring operation of the diagnostic systems and scheduling servicing of hardware, firmware, and software within the systems to minimize down time. Currently, field service engineers are often in frequent contact with medical institutions for servicing of diagnostic systems, or are available on an as-needed basis. Increasingly, however, it has become desirable to allow field service technicians to address certain service needs remotely, such as through network connections or conventional voice communication with the medical institutions.

In one approach to remote servicing of medical diagnostic systems, an automated service center can be placed in direct communication with subscribing systems, such as via an open network connection or a virtual proprietary network. The automated service center can access operational data from the diagnostic systems and use the data to evaluate the operating state of the systems, as well as to anticipate possible service needs. Information relating to the state of the systems can then be communicated to the institution or to field service engineers through network connections or by telephone.

Remote service arrangements of this type offer distinct advantages over more conventional on-site servicing. For example, they permit the service technicians to more readily access operating state information both at the initiation of the service center and upon request by the medical institution in which the diagnostic system is installed. They also provide a relatively transparent service strategy in which system operators are not required to intervene for the transmission of operational or service data needed to respond to their requests. Similarly, they permit detection of yet unidentified service needs without distracting the medical institution personnel from their normal tasks.

However, there is still need for further improvement in remote service arrangements for medical diagnostic equipment. There is a need, for example, for an improved or streamlined strategy for identifying service request types which can be submitted by field service engineers and used as the basis for acquiring and processing data from the diagnostic systems, such as via an automated service center. Such techniques would greatly enhance the ability of the field service technicians to operate autonomously, while allowing data to be acquired and processed based upon requests from a field service technician without actually requiring the technician to directly contact the diagnostic systems, wait for the data transfer, or to rely on intervention of another service technician at the remote service center, which can result in even greater delay or downtime.

SUMMARY OF THE INVENTION

The invention provides a novel technique for remotely servicing medical diagnostic systems designed to respond to these needs. The technique may be employed with one or a range of diagnostic system modalities. The diagnostic systems are accessible by a service facility through network connections which may be of various types, including open and proprietary networks. A field service technician is equipped with an interface unit, such as a laptop computer, through which service request modules may be identified and transmitted to the service facility, such as through an electronic message. The service request modules may include a wide variety of standard requests, depending upon the specific system modality and configuration. The service technician may select the service request from a menu, thereby alleviating the need to predefine or memorize available standard requests. The standard request menu may be expandable over time as additional data types or processed data presentations become available. In response to the message from the field service technician, the service facility contacts the identified diagnostic system and accesses the information required by the service technician. This process may be fully automated to expedite handling without human intervention. Data or reports may then be compiled and re-transmitted to the service technician via electronic messages in response to the request.

BRIEF DESCRIPTION OF THE DRAWINGS

FIG. 3 is a flow chart indicating exemplary steps in the generation of service requests, transmission of the service requests, and handling of the service requests in accordance with the data flow in FIG. 2; and, FIG. 4 is a diagram illustrating an exemplary series of pre-established service request menus from which the field technician may select modules for various systems and modalities.

DETAILED DESCRIPTION OF THE INVENTION

Figure 1:
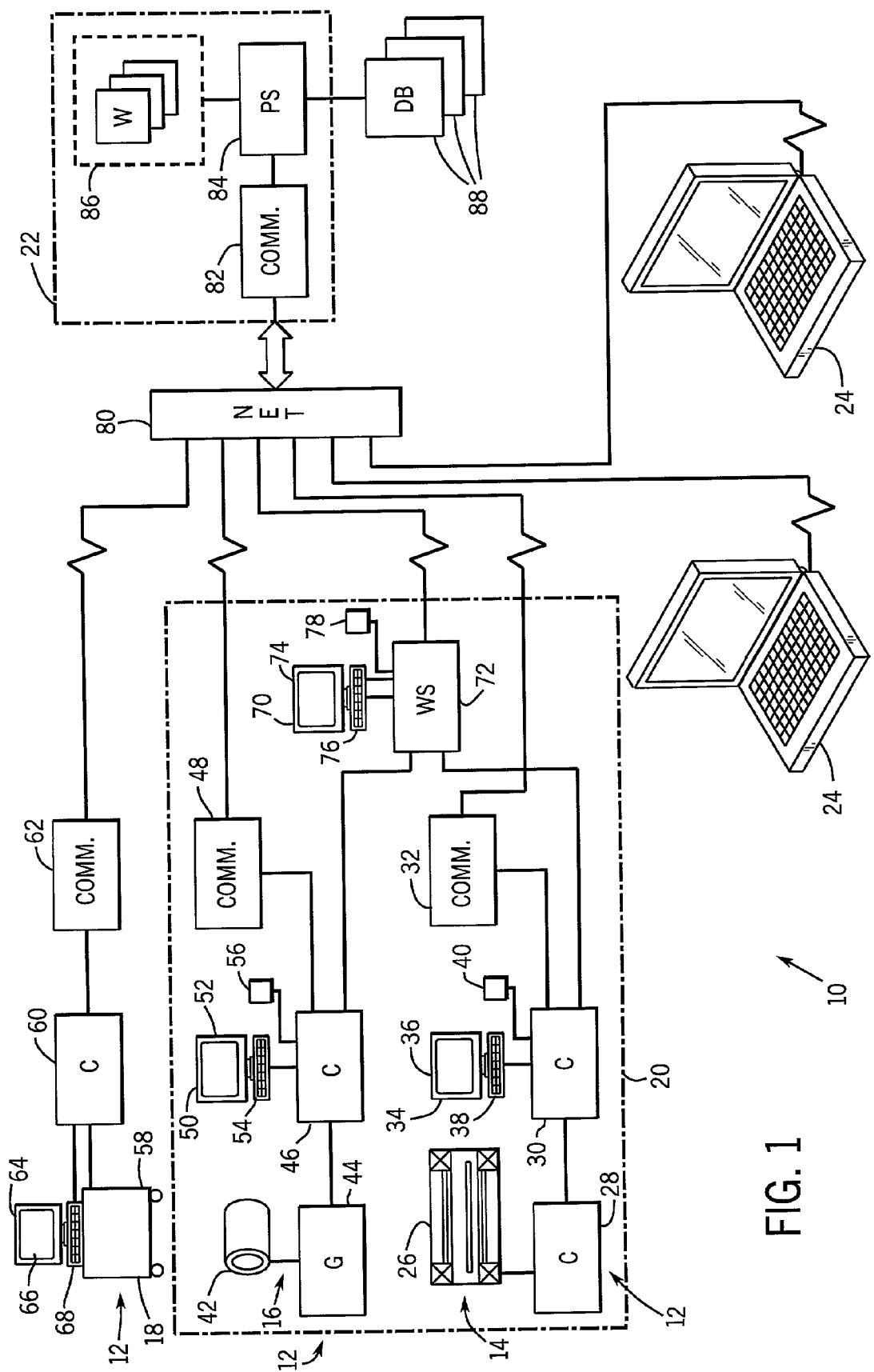
FIG. 1 is a diagrammatical representation of a series of medical diagnostic systems coupled to a remote service facility and, therethrough, to field service technician stations for providing remote service to the diagnostic systems in accordance with certain aspects of the present invention.

Turning now to the drawings, and referring first to FIG. 1, a service system 10 is illustrated for providing remote service to a plurality of medical diagnostic systems 12. In the embodiment illustrated in FIG. 1, the medical diagnostic systems include a magnetic resonance imaging (MRI) system 14, a computed tomography (CT) system 16, and an ultrasound imaging system 18. Other types and modalities of equipment may, of course, be included in the service system. The diagnostic systems may be positioned in a single location or facility, such as a medical facility 20, or may be remote from one another as shown in the case of ultrasound system 18. The diagnostic systems are serviced from a centralized service facility 22. Moreover, a plurality of field service units 24 may be coupled in the service system for transmitting service requests, verifying service status, transmitting service data and so forth as described more fully below.

In the exemplary embodiment of FIG. 1, several different system modalities are provided with remote service by the service facility. These and other modalities may be similarly serviced by the service facility, depending upon the capabilities of the service facility, the types of diagnostic systems subscribing to service contracts with the facility, as well as other factors. In general, however, the present technique is particularly well suited to providing remote service to a wide variety of medical diagnostic system modalities, including MRI systems, CT systems, ultrasound systems, positron emission tomography (PET) systems, nuclear medicine systems, and so forth. Moreover, the various modality systems serviced in accordance with the present techniques may be of different type, manufacture, and model. Service requests and data transmitted between the systems and the service facility include data for identifying the type and modality of the serviced system, as well as data specifically adapted to the system modality and model. It should also be noted that, as used herein, the term "service request" is intended to include a wide range of inquiries, comments, suggestions and other queries or messages generated by a diagnostic system, an institution in which a system is disposed or managed, or a field service technician via a field service unit 24. In particular, such requests may relate to problems occurring on systems, applications questions, questions of a general nature, questions relating to financial or subscription arrangements, information sharing, reports, applications, protocols, system software patches, configuration modifications, and so forth. In a presently preferred embodiment, pre-established service functions may be requested from lists established by a service facility. The requests are then transmitted, screened and handled automatically by the service facility. The requests may require acquisition, processing and transfer to the field service unit of operational or historical data, or may, for example, require the service facility to transmit data to or reconfigure a subscribing diagnostic system.

Depending upon the modality of the systems, various subcomponents or subsystems will be included. In the case of MRI system 14, such systems will generally include a scanner 26 for generating pulsed magnetic fields and for collecting signals from emissions by gyromagnetic material within a subject of interest. The scanner is coupled to a control and signal detection circuit 28 which, in turn, is coupled to a system controller 30. System controller 30 includes a platform for exchanging service requests, messages and data with service facility 22 as described more fully below. The platform may vary according to the system type, and the present technique may accommodate a variety of platforms without requiring the field service technician to know, in advance, what platform is active on the system. System controller 30 is linked to a communications module 32, which may be included in a single or separate physical package from system controller 30. System controller 30 is also linked to an operator station 34 which will typically include a computer monitor 36, a keyboard 38, as well as other input devices 40, such as a mouse. In a typical system, additional components may be included in system 14, such as a printer or photographic system for producing reconstructed images based upon data collected from scanner 14. Although reference is made herein generally to "scanners" in diagnostic systems, that term should be understood to include medical diagnostic data acquisition equipment generally, not limited to image data acquisition, as well as to picture archiving communications and retrieval systems, image management systems, facility or institution management systems, viewing systems and the like, in the field of medical diagnostics. More particularly, equipment benefiting from the present techniques may include imaging systems, clinical diagnostic systems, physiological monitoring systems and so forth.

Similarly, CT system 16 will typically include a scanner 42 which detects portions of x-ray radiation directed through a subject of interest. Scanner 42 is coupled to a generator and controller, as well as to a signal acquisition unit, represented collectively at reference numeral 44, for controlling operation of an x-ray source and gantry within scanner 42, and for receiving signals produced by a detector array moveable within the scanner. The circuitry within the controller and signal acquisition components is coupled to a system controller 46 which, like controller 30 mentioned above, includes circuitry for commanding operation of the scanner and for processing and reconstructing image data based upon the acquired signals. System controller 46 is linked to a communications module 48, generally similar to communications module 32 of MRI system 14, for transmitting and receiving data for remote service of system 16. Also, system controller 46 is coupled to an operator station 50 which includes a computer monitor 52, a keyboard 54, as well as other input devices 56, such as a mouse. Moreover, like MRI system 14, CT system 16 will generally include a printer or similar device for outputting reconstructed images based upon data collected by scanner 42.

Other modality devices will include circuitry and hardware particularly configured for acquiring or producing signals in accordance with their particular physics and design. In particular, in the case of ultrasound system 18, such systems will generally include a scanner and data processing unit 58 for transmitting ultrasound signals into a subject of interest, and for acquiring resultant signals which are processed for reconstructing a useful image. The system includes a system controller 60 which regulates operation of scanner 58 and which processes acquired signals to reconstruct the image. Moreover, system 18 includes a communications module 62 for transmitting service requests, messages and data between system controller 60 and service facility 22. System 18 also includes an operator station 64, including a monitor 66, as well as input devices such as a keyboard 68.

Where more than one medical diagnostic system is provided in a single facility or location, as indicated in the case of MRI and CT systems 14 and 16 in FIG. 1, these may be coupled to a management station 70, such as in a radiology department of a hospital or clinic. Where such a management station is provided, it may be linked directly to controllers for the various diagnostic systems, such as controllers 30 and 46 in the illustrated embodiment. The management system may include a computer workstation or personal computer 72 coupled to the system controllers in an intranet configuration, in a file sharing configuration, a client/server arrangement, or in any other suitable manner. Moreover, management station 70 will typically include a monitor 74 for viewing system operational parameters, analyzing system utilization, and exchanging service requests and data between the facility 20 and the service facility 22. Input devices, such as a standard computer keyboard 76 and mouse 78, may also be provided to facilitate the user interface. It should be noted that, alternatively, the management system, or other diagnostic system components, may be "stand-alone" or not coupled directly to a diagnostic system. Similarly, in certain applications, a diagnostic system may consist of a stand-alone or networked picture archiving and communication system or a viewing station provided with some or all of the functionality described herein.

The communication modules mentioned above, as well as workstation 72 and field service units 24 may be linked to service facility 22 via a remote access network 80. For this purpose, any suitable network connection may be employed. Presently preferred network configurations include both proprietary or dedicated networks, as well as open networks, such as the Internet. Data may be exchanged between the diagnostic systems 12, field service units 24, and remote service facility 22 in any suitable format, such as in accordance with the Internet Protocol (IP), the Transmission Control Protocol (TCP), or other known protocols. Moreover, certain of the data may be transmitted or formatted via markup languages such as the HyperText Markup Language (HTML), or other standard languages.

Within service facility 22, messages, service requests and data are received by communication components as indicated generally at reference numeral 82. Components 82 transmit the service data to a service center processing system, represented generally at reference numeral 84 in FIG. 1. The processing system manages the receipt, handling and transmission of service data to and from the service facility. In general, processing system 84 may include one or a plurality of computers, as well as dedicated hardware or software servers for processing the various service requests and for receiving and transmitting the service data as described more fully below. Service facility 22 also includes a bank of operator workstations 86 which may be staffed by service engineers who address service requests and provide off and on-line service to the diagnostic systems, where necessary. In the present technique, however, field service engineers may have their standard service requests handled entirely automatically without intervention of the service engineers at the workstations. Also, processing system 84 may be linked to a system of databases or other processing systems 88 at or remote from the service facility 22. Such databases and processing systems may include extensive database information on operating parameters, service histories, and so forth, both for particular subscribing equipment or institutions, as well as for extended populations of diagnostic equipment. As described below, such databases may be employed both for servicing of particular diagnostic systems and for tracking such servicing, as well as for deriving comparison data for use in servicing a particular system or a family of systems.

Each field service unit 24 is equipped for the exchange of data directly with service facility 22, or with medical diagnostic systems 12 through service facility 22. In a presently preferred embodiment, each field service unit 24 includes a laptop computer on which functional software or code is installed for compiling specific requests for service in accordance with pre-established menus of service modules. Such code may include any suitable format, such as a graphical user interface on which the menus appear. Moreover, each field service unit is equipped for transmission and receipt of data in formats which may be different from those employed for the exchange of data with the diagnostic systems. Specifically, each field service unit is equipped to formulate, transmit, receive and display electronic messages and web pages to define specific service requests and to display the results of service inquiries executed automatically by the service facility 22. As noted above, the interface, protocols and displays provided on the field service unit may be different from one or all of those of the systems served by the unit and the service facility.

In accordance with certain aspects of the present technique, field service engineers equipped with the field service units 24 will typically be assigned specific medical diagnostic systems or institutions to which service is provided or subscribed. The field service engineer may, from time to time, physically visit the equipment or institutions for on-site servicing needs. However, between or during such visits, the field service engineer may request specific data regarding the operational state of the equipment via the field service units 24.

Figure 2:
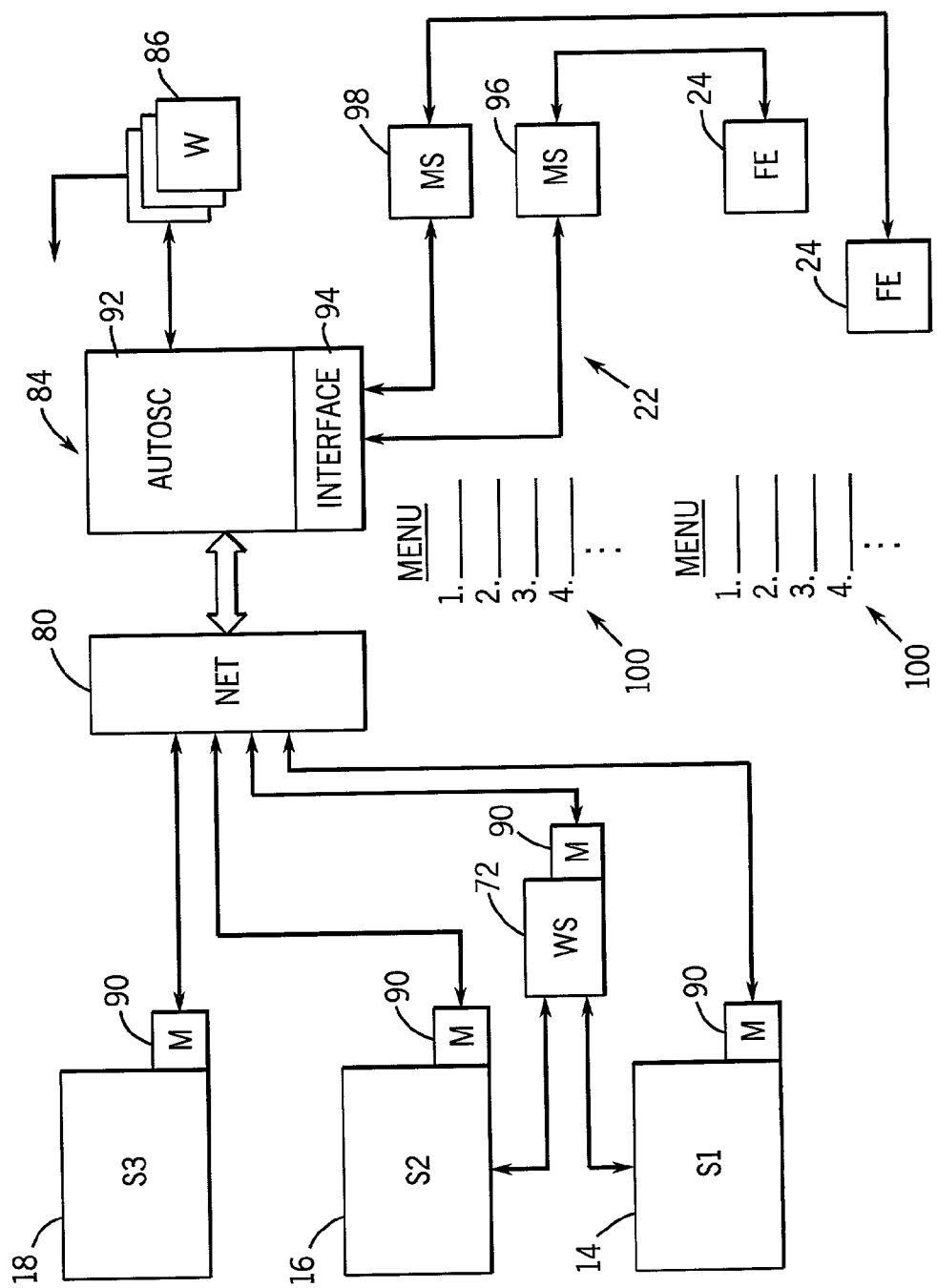
FIG. 2 is a signal flow diagram indicating typical flow of data between the components of FIG. 1 in requesting, accessing, and compiling service data.

FIG. 2 illustrates a typical data flow diagram for composing, transmitting and handling of service requests from field service units 24 in an automated fashion. While certain of the functions requested by the field service units may be handled by human operators, such as service engineers in facility 22 or by operators within the institution in which a medical diagnostic system of interest is situated, in the diagram of FIG. 2, the service functions requested by the field service units, are handled in a completely automated manner. That is, service requests are composed including identification of a predefined service function from a menu, and identification of a particular medical diagnostic system of interest. The service request may be stored on the field service unit, and is ultimately transmitted via a network link to the service facility. The service facility then verifies validity of the service request and, if found valid, executes the request by accessing the required operational data, compiling any required reports, and so forth. The results of the service function are then transmitted back to the field service unit requesting the function.

In the diagram of FIG. 2, the diagnostic systems discussed above are represented as blocks 14, 16 and 18. Each block includes network communication hardware and software, such as a modem 90. Where the systems are linked in an intranet-type arrangement, as shown for systems 14 and 16, a similar communications arrangement 90 is provided for the work station or management station 72. All of the systems, and the management station, may be linked to the service facility 22 via network 80. Within the service facility 22, an automated service module, designated generally at reference numeral 92 in FIG. 2, receives and processes at least certain of the service requests received either from the diagnostic equipment or from the field service units 24. In the case of the field service units, such requests are channeled through an interface module 94 which may serve functions of deciphering and validating service requests as described more fully below. The automated service module 92 preferably includes a server for receiving and processing service requests in one of several call handling strategies, such as a first-in, first-out queue sequence. Moreover, the automated service module 92 may be linked to work stations 86, permitting service engineers at the service facility to view, monitor, and intervene in the handling of certain of the service requests.

The field service units 24 are coupled to the automated service module 92, and its interface module 94, through one or more mail servers 96 and 98. Mail servers 96 and 98 receive electronic messages including service requests from the field service units 24, and store the service requests for transmission to the automated service module 92. Moreover, mail servers 96 and 98 store response messages produced by the automated service module after execution of service functions defined in the service request. In a presently preferred arrangement, service requests are transmitted to and from the field service units by a conventional electronic messaging arrangement, wherein the field service units include designated addresses and passwords for accessing stored response messages and for transferring data included in the response messages upon demand.

Also as indicated in FIG. 2, the field service units 24 and the automated service module 92 each preferably include appropriate code defining a menu of available service functions, as represented at reference numeral 100 in FIG. 2. It has been found that the use of such menus provides a generally sufficient basis for a wide variety of standard service requests responding to typical needs of the field service personnel. Moreover, the presentation of the menu at the field service unit 24, such as in a graphical format, facilitates selection of the standard functions in composing the service request. While in a present embodiment lists of standard requests are available via simple textual presentations, various menu configurations may be employed. As additional functions are added to the available menu, these can be downloaded to the field service units during normal connect sessions, or via electronic messages. It should be noted, however, that the service facility may make additional standard requests or functionalities available without necessarily standardizing or conforming all field service units, thereby facilitating expansion of the remote serviceability offered by the present technique. Of course, additional service requests can be composed by the field service units which are not part of the standard menu. However, such customized service requests may be handled in a conventional manner, such as through intervention of a service engineer at the service facility.

FIG. 3 identifies a sequence of steps in exemplary control logic for composing and executing service requests through the flow of FIG. 2. As shown in FIG. 3, the logic, designated generally by reference numeral 102, begins at step 104 with the formulation of a service request. As indicated above, the service request is formulated at the field service unit 24 and will typically include identification of at least one of the standard service functions from a menu 100, as well as identification of one or more particular medical diagnostic systems of interest. In addition, where desired, such service requests may include broader system identification data, such as for requesting performance parameters for a family, series, type or population of systems. A field service engineer may therefore request information relating to operation of a specific system, or a group of systems in a specific facility, or a group of systems for which the engineer provides service.

At step 106, the service request formulated at step 104 is transmitted to a mail server, such as server 96 in FIG. 2. The mail server stores the service request and eventually transmits the request to the automated service module 92, such as via interface module 94. Subsequent steps identified in FIG. 3 may be performed at various locations in the diagram of FIG. 2. For example, either at the mail server or in interface module 94, a security check may be performed as indicated at step 108. In a present embodiment, service requests may be received only from recognized field service modules and with established access codes. Thus, at step 108 the originating source of the request is compared with a list or index of permitted sources and, if the requesting source is not authorized to request the service, a notification message is sent as indicated at step 110. If, on the other hand, the requesting source is authorized to submit the request, the logic proceeds to step 112. It should be noted that the security check performed at step 108 may include additional levels of security. For example, certain field service engineers may be provided with access to specific levels of service or operational data while other service personnel may be restricted from such access.

At step 112 the service request is evaluated to determine its validity. Again, various types of validity verifications may be performed at step 112. For example, in a present embodiment, the field service units may be configured to request various types of service functions to be performed for various system modalities. Note, again, that the list of available standard service requests may or may not be visible on the field service unit itself, facilitating expansion of the available request repertoire without the need to conform all field service units. Certain of the service functions may be specifically adapted to the modalities. For example, inquiries into performance of x-ray tubes may be defined in the menus, but only permitted for systems including such tubes, such as CT systems and x-ray systems. Similarly, service functions including operational data relating to temperatures and cryogen levels may be defined in the service menus, but may be applicable to a limited range of diagnostic systems, such as MRI systems. Thus, at step 112, interface module 94 may evaluate the service request to verify that the requested function is able to be performed for the identified diagnostic system. This verification step may include accessing system data, such as from a database of the type discussed above with reference to FIG. 1, including data regarding the system type, system modality, and so forth. If the service request is not valid, a notification message is formulated at step 114, and retransmitted to the field service unit through the intermediary of the mail servers. If the request is found valid at step 112, logic proceeds to step 116.

At step 116 the automated service module 92 generates a request acknowledgment message and transmits the message to the field service unit requesting service. At step 118 the request is placed in a queue for automatic handling by the automated service module. When the service request reaches the top of the queue it is handled by the automated service module. At step 120 the identified medical diagnostic system is contacted, such as via a network link. The contact made at step 120 is preferably entirely automated. That is, the communications modules included in the service facility contact the diagnostic system or the facility in which the system is installed, establish a data connection and proceeds with the service functions requested. It should be noted, however, that certain types of service functions may not require accessing a specific system, but may necessitate accessing data from a database within the service facility or remote from the service facility. For example, the field service engineer may request a standard service function for compiling a report of service provided to a diagnostic system or facility over a predetermined time period. Such data may be included in a database at the service facility. Similarly, certain service functions may require both data from the diagnostic system as well as data in such databases. For example, comparisons of x-ray tube performance, and reports based upon the comparisons may be compiled based upon both actual performance data from a CT or x-ray system, as well as data contained in extensive databases for entire populations of comparable systems.

At step 122 in FIG. 3 the data required for execution of the requested service function is identified and accessed. In a typical service function, step 122 may include identification of log files, error files, image files (both raw and processed), and so forth. The required data is transmitted to the service facility for processing as indicated at step 124. Of course, certain of the processing steps may be performed at the diagnostic equipment or facility where appropriate routines are available at those locations. Moreover, the processing steps performed at step 124 may include translation of data files from one format to another, such as to the DICOM format used as a standard in many medical imaging systems, as well as compression of data files for storage or transmission. Similarly, where the service function to be performed includes compilation of a report, such as a status report on the operational state of a system, such reports may be formatted at step 124.

At step 126 the requested data is transmitted to the requesting field service unit through the intermediary of a mail server 96 or 98. The response may include raw or tabulated data, as well as reports generated based upon the accessed data. Moreover, depending upon the distribution scenario desired, such reports or service responses may be transmitted directly with an electronic message to the requesting party, such as in an appended file, or may be made available to be "pulled" at a convenient time.

As noted above, a wide range of standard service modules or functions may be made available to the field service units in accordance with the present technique. FIG. 4 illustrates a series of module groups 128 which may be defined for a corresponding series of system modalities. For example, a first group 130 includes a menu of modules for performing service functions for a first modality, such as MRI systems. Other groups 132 and 134 provide menus for other modalities, such as CT and x-ray systems. Thus, the field service technician may request predefined service functions for a variety of systems for which he provides service.

Within each group of service modules, specific functions may be defined by brief descriptions. Certain of the service functions in each group may be similar or identical, while others may be specifically adapted to the modality of the diagnostic systems. For example, as indicated by reference numeral 136 in FIG. 4, a first service module may constitute a connectivity verification in which the automated service module of the service facility will simply establish a network link with a designated system to verify the operability of the network connection and related hardware and software. Such service functions may be essentially identical regardless of the modality of the system of interest. On the other hand, other service modules, which may be associated in subgroups by the type of function performed, may be applicable only to certain modality types, as indicated by reference numerals 138, 140 and 142 in FIG. 4. In a present embodiment illustrated, such subgroups may include various specific data gathering operations as well as specific reporting operations.

It should be noted that the foregoing technique may permit field service units to submit and have executed standard service requests and functionalities on a wide variety of systems, not only of different modality, but of different manufacture, type, configuration, and so forth. The automated handling of the service requests thereby facilitates interaction of the field service technicians, via the field service units, with any system to which the service facility can connect and interact. It should also be noted that a wide variety of adaptable configurations may be associated with the service requests. For example, while service requests may be handled on a first-in, first-out basis, where desired, the certain requests may be accompanied by a specific execution schedule (e.g. date and time), such as following a specific day of the week, or at a time when the diagnostic equipment is less likely to be occupied by examinations. Similarly, certain requests may include regular or periodic schedules whereby the request is executed automatically on a periodic basis (e.g. daily, weekly, monthly, etc.). Moreover, certain requests may direct responses to one or more recipients other than the requesting field service unit.

The invention claimed is:

1. A system for providing field service to medical diagnostic equipment, the system comprising:
   a medical diagnostic station configured to store medical image data;
   a field service unit configured to generate service requests for operational servicing of the medical diagnostic station, identifying a standard service function from a plurality of service functions and a unique identifier for the medical diagnostic station; and
   a service facility configured to be coupled to the medical diagnostic station and to the field service unit via network links, the service facility including a service request management device for receiving the service requests from the field service unit, accessing data stored at the medical diagnostic station as defined by the standard service function, and transmitting data to the field service unit in response to the service request.

2. The system of claim 1, comprising a plurality of medical diagnostic stations of different modalities, and wherein the standard service functions of the service requests include modality-specific functions.

3. The system of claim 1, wherein the field service unit is configured to transmit the service request via an electronic message to the service facility, and the service facility is configured to transmit the data to the field service unit via an electronic response message.

4. The system of claim 1, wherein the service facility is configured to verify consistency between components of the service requests received from the field service unit prior to accessing the data from the medical diagnostic system.

5. The system of claim 1, further comprising at least one database for storing historical service data for the diagnostic station, and wherein the service facility is configured to access the historical service data for response to the service request from the field service unit.

6. The system of claim 1, wherein the service facility is configured to receive the service request, access the data from the diagnostic system and transmit the data to the field service unit automatically and without operator intervention.

7. The system of claim 1, wherein the plurality of service functions are defined by a list on the field service unit.

8. A system for accessing operational data from a medical diagnostic station, the system comprising:
- an automated service facility including a server configured to recognize and execute a plurality of predefined service functions, the service functions each including accessing operational data for a medical diagnostic station; and
- a field service unit configured to be coupled to the automated service facility via a network link, to generate service requests, and to transmit the service requests to the automated service facility for operational servicing of the medical diagnostic station, each service request including identification of a predefined service function and an identification of at least one medical diagnostic station.

9. The system of claim 8, wherein the automated service facility is configured to establish a network link with a medical diagnostic station identified in a service request received from the field service unit, and to access operational data from the medical diagnostic station in accordance with a service function identified in the service request.

10. The system of claim 8, wherein the automated service facility is coupled to at least one database and access the operational data at least partially from the at least one database.

11. The system of claim 8, wherein the server is configured to transmit service data to the field service unit in response to the service request after executing the service function identified in the service request.

12. The system of claim 8, wherein the predefined service functions include modality-specific functions.

13. The system of claim 12, wherein the predefined service functions include functions specific to magnetic resonance imaging systems.

14. The system of claim 12, wherein the predefined service functions include functions specific to x-ray imaging systems.

15. The system of claim 12, wherein the predefined service functions include functions specific to x-ray imaging systems.

16. A method for remotely obtaining operational data from a medical diagnostic station, the method comprising the steps of:
- composing a service request on a field service unit, the service request including identification of a service function from a plurality of predefined service functions and a medical diagnostic system of interest, the service request relating to operational servicing of the medical diagnostic system;
- transmitting the service request to an automated service facility;
- accessing operational data from the medical diagnostic system of interest via the automated service facility as defined by the at least one service function; and
- transmitting data based on the accessed data from the automated service facility to the field service unit.

17. The method of claim 16, comprising the further step of verifying the service request at the automated service facility prior to accessing the operational data.

18. The method of claim 17, wherein the step of verifying includes verifying that the service function identified in the service request is valid for the medical diagnostic system of interest.

19. The method of claim 16, wherein the operational data is accessed from the medical diagnostic system of interest.

20. The method of claim 16, wherein the data is transmitted to the field service unit via an electronic message stored on an electronic message server.

21. The method of claim 16, wherein the step of composing a service request includes the step of selecting a service function from a menu of the plurality of predefined service functions.

22. The method of claim 16, wherein the plurality of predefined service functions includes at least one service function common to a plurality of medical diagnostic system modalities.

23. A method for providing remote service to a plurality of medical diagnostic systems, the method comprising the steps of:
- establishing a menu of predefined service functions;
- composing a service request on a field service unit for operational servicing of a medical diagnostic system of interest, the service request including identification of at least one of the predefined service functions and the medical diagnostic system of interest;
- transmitting the service request to an automated service facility;
- executing the service function for the medical diagnostic system of interest; and
- transmitting a response message to the field service unit.

24. The method of claim 23, wherein the menu of predefined service functions includes functions specific to a desired medical diagnostic system modality.

25. The method of claim 23, comprising the further step of verifying validity of the service function identified in the service request for the medical diagnostic system of interest.

26. The method of claim 23, wherein the automated service facility is configured to receive the service request, execute the service function and transmit the response message without operator intervention.

27. The method of claim 23, wherein the step of executing the service function includes establishing a network link between the automated service facility and the medical diagnostic system of interest and transmitting operational data from the medical diagnostic system of interest to the automated service facility.

28. The method of claim 23, wherein the response message includes a report of results of the service function.

* * * * *